US00PP35359P3

(12) United States Plant Patent
Bull

(10) Patent No.: US PP35,359 P3
(45) Date of Patent: Aug. 29, 2023

(54) ***ECHINACEA* PLANT NAMED 'BULLECHIPUR 108'**

(50) Latin Name: *Echinacea purpurea*
Varietal Denomination: BullEchipur 108

(71) Applicant: Hartwig Bull, Gönnebek (DE)

(72) Inventor: Hartwig Bull, Gönnebek (DE)

(73) Assignee: Hartwig Bull, Gönnebek (DE)

( * ) Notice: Subject to any disclaimer, the term of this patent is extended or adjusted under 35 U.S.C. 154(b) by 0 days.

(21) Appl. No.: 17/974,158

(22) Filed: Oct. 26, 2022

(65) Prior Publication Data

US 2023/0140851 P1 May 4, 2023

Related U.S. Application Data

(60) Provisional application No. 63/360,789, filed on Oct. 28, 2021.

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
See application file for complete search history.

*Primary Examiner* — Susan McCormick Ewoldt
(74) *Attorney, Agent, or Firm* — The Webb Law Firm

(57) ABSTRACT

A new and distinct variety of *Echinacea* plant having a compact growth habit and numerous, lavender-pink colored blooms.

1 Drawing Sheet

Botanical classification: *Echinacea purpurea.*
Varietal denomination: 'BullEchipur 108'.

BACKGROUND OF THE INVENTION

The present invention comprises a new and distinct cultivar of *Echinacea* plant known by the varietal name 'BullEchipur 108'. The new variety was discovered in August of 2019 in Gönnebek, Germany as the result of a planned breeding program with the purposes of providing *Echinacea* plants with unique flower colors, a compact growth habit, increased branching, and more uniformity when compared to prior *Echinacea* plants. The new variety is the result of a cross between an unpatented *Echinacea purpurea* variety from the internal breeder's reference of "Bul 2015-138" (female parent) and open pollination from a collection of unpatented *Echinacea purpurea* varieties referred to as "Bul Mix 04-2016" from the breeder's own collection. As such, the exact male parent from this collection is unknown. The new variety was first asexually reproduced via in-vitro tissue culture cuttings in Gönnebek, Germany in September of 2019. The new variety is similar to its parental varieties in botanical classification, but exhibits a more compact growth habit and different flower color than both of its parental varieties. The ray florets of the female parent are hot pink in color (close to Red-Purple Group RHS 68B) and the ray florets of the possible male parents are pink in color. Further, 'BullEchipur 108' exhibits better branching than its female parent and smaller leaves than any of its possible male parents.

When 'BullEchipur 108' is compared to *Echinacea purpurea* variety named 'Amazing Dream' (U.S. Plant Pat. No. 23,019), 'BullEchipur 108' is similar to 'Amazing Dream' in botanical classification and flower color, but 'BullEchipur 108' exhibits a more compact growth habit with less branching ('Amazing Dream' has approximately 50 flower stems) and fewer flowers ('Amazing Dream' has 1-3 inflorescences per stem) that distinguish it from 'Amazing Dream'. Further, the following characteristics distinguish 'BullEchipur 108' when generally compared to other *Echinacea* varieties known to the breeder:

Lavender-pink flower color;
High flower number per plant;
A very compact and uniform growth habit;
High branching;
Fast crop time; and
Small leaves.

The new variety has been trial and field tested and has been found to retain its distinctive characteristics and remain true to type through successive asexual propagations. The present invention has not been evaluated under all possible environmental conditions. The phenotype may vary with variations in environment without a change in the genotype of the plant.

DESCRIPTION OF THE DRAWINGS

The accompanying photographic drawing illustrates the new variety at 22 weeks of age, with the color being as nearly true as is possible with color illustrations of this type:

FIG. 1 shows an entire plant of the new variety.

DESCRIPTION OF THE PLANT

The following detailed description sets forth the characteristics of the new variety as the result of asexual reproductions performed via in vitro tissue culture cuttings carried out in Gönnebek, Germany. Plants of the new variety were grown outdoors in 19 cm (3 liter) pots under normal field production conditions, and the color readings and measurements were observed outdoors under natural light on 22 week old plants in Gönnebek, Germany. Color references are primarily to The 2015 R.H.S. Colour Chart of The Royal Horticultural Society of London, Sixth Edition, except where terms of ordinary significance are used.

PLANT

Time to initiate roots: About 7 days at approximately 19-20° C.

Time to develop roots: About 40-50 days at approximately 18° C.

Time to produce a finished flowering plant from a rooted cutting: About 12-14 weeks in a 19 cm container.

Rooting habit: Exhibits numerous roots that are freely branching and healthy in appearance.

Plant height: 45.0-50.0 cm.

Plant width: 25.0-30.0 cm.

Habit: Upright, compact, and uniform growth with numerous branches.

Disease/pest resistance: Nothing unusual noted to date.

Temperature tolerance: Nothing unusual noted to date.

Drought tolerance: Average.

Branches (flowering stems):

*Number per plant.*—15-35.

*Length.*—20.0-30.0 cm.

*Diameter.*—3.0-10.0 mm.

*Internode length.*—1.0-5.0 cm.

*Angle.*—Upright and outward.

*Strength.*—Strong.

*Texture.*—Pubescence present.

*Color.*—Close to Yellow-Green Group RHS 146A.

Foliage:

*Arrangement.*—Single.

*Leaf.*—Length: 4.0-14.0 cm. Width: 1.0-3.0 cm. Shape: Lanceolate. Apex: Acuminate. Base: Attenuate to acute. Margin: Entire. Aspect: Straight to curved. Texture: Upper surface: Rough. Lower surface: Rough. Color: Young leaves: Upper surface: Close to Green Group RHS 137A. Lower surface: Close to Green Group RHS 137C. Mature leaves: Upper surface: Close to Green Group RHS 137A. Lower surface: Close to Green Group RHS 137C. Petiole: None present. Veins: Venation type: Cross-venulate to longitudinal. Color: Upper surface: Close to Yellow-Green Group RHS 145A. Lower surface: Close to Yellow-Green Group RHS 145B.

INFLORESCENCE

Bud:

*Diameter.*—1.0-3.0 cm.

*Length.*—1.3-2.0 cm.

*Color.*—Close to Green Group RHS N137C.

Appearance: Elliptic-shaped ray florets and tubular-shaped disc florets.

Natural flowering season: Flowering occurs from July-September in Gönnebek, Germany, beginning approximately 12-14 weeks after planting.

Average number of inflorescences per plant: 20-35.

Average number of inflorescences per branch: 1-2.

Disc and ray floret arrangement: Disc florets are arranged in the middle of the receptacle of the composite, single, freely flowering plant, with ray florets extending outwardly therefrom.

Fragrance: Very light and sweet.

Inflorescence:

*Diameter.*—4.0-8.0 cm.

*Height (depth).*—2.0-3.5 cm.

*Diameter of disc.*—1.5-3.0 cm.

*Receptacle height.*—1.0 cm.

*Receptacle diameter.*—1.5-3.5 cm.

Ray florets:

*Number per inflorescence.*—18-30.

*Arrangement.*—In two or three whorls.

*Length.*—2.0-3.5 cm.

*Width.*—1.2-1.8 cm.

*Shape.*—Elliptical.

*Apex.*—Obtuse.

*Base.*—Acute.

*Margin.*—Entire.

*Texture.*—Upper surface: Smooth and glabrous. Lower surface: Rough.

*Color.*—When opening: Upper surface: Close to Purple Group RHS 75B to 75A. Lower surface: Close to Purple Group RHS 75C. At maturity: Upper surface: Close to Purple Group RHS 75B to 75A. Lower surface: Close to Purple Group RHS 75C. Ground color description: Close to Purple Group RHS 75B to 75A.

*Venation.*—Appearance: Parallel. Color: Upper surface: Same color as the florets. Lower surface: Same color as the florets.

Disc florets:

*Number per inflorescence.*—Numerous; too many to quantify.

*Arrangement.*—In the center of receptacle.

*Length.*—8.0-15.0 mm.

*Width.*—1.0-2.0 mm.

*Shape.*—Tubular.

*Apex.*—Pointed.

*Color.*—Immature: Close to Greyed-Purple Group RHS 187C. At maturity: Close to Greyed-Purple Group RHS 187C.

Phyllaries:

*Number per inflorescence.*—40-50.

*Arrangement.*—In three to four whorls.

*Length.*—Approximately 1.0 cm.

*Width.*—2.0-4.0 mm.

*Shape.*—Lanceolate.

*Apex.*—Elongated oval.

*Base.*—Fused.

*Margin.*—Entire.

*Texture.*—Upper surface: Rough. Lower surface: Rough.

*Color.*—Immature: Upper surface: Close to Green Group RHS NN137C. Lower surface: Close to Green Group RHS NN137C. At maturity: Upper surface: Close to Green Group RHS NN137C. Lower surface: Close to Green Group RHS NN137C.

Reproductive organs:

Androecium:

*Presence.*—On disc florets.

*Number (per floret).*—One.

*Filament length.*—1.0-2.0 mm.

*Filament color.*—Red-brown.

*Anther.*—Shape: Oval. Length: 1.0 mm. Color: Red-brown.

*Pollen.*—Color: Close to Yellow-Orange Group RHS 15B. Amount: Plentiful — too much to quantify.

Gynoecium:

*Presence*.—In disc and ray florets.

*Pistil length*.—1.0-2.0 mm.

*Stigma*.—Shape: Two-parted. Color: Red-brown.

*Style*.—Length: 1.0-2.0 mm. Color: Red-brown.

Seeds:

*Overall size*.—1.0-2.0 mm.

I claim:

1. A new and distinct variety of *Echinacea* plant named 'BullEchipur 108', as is herein illustrated and described.

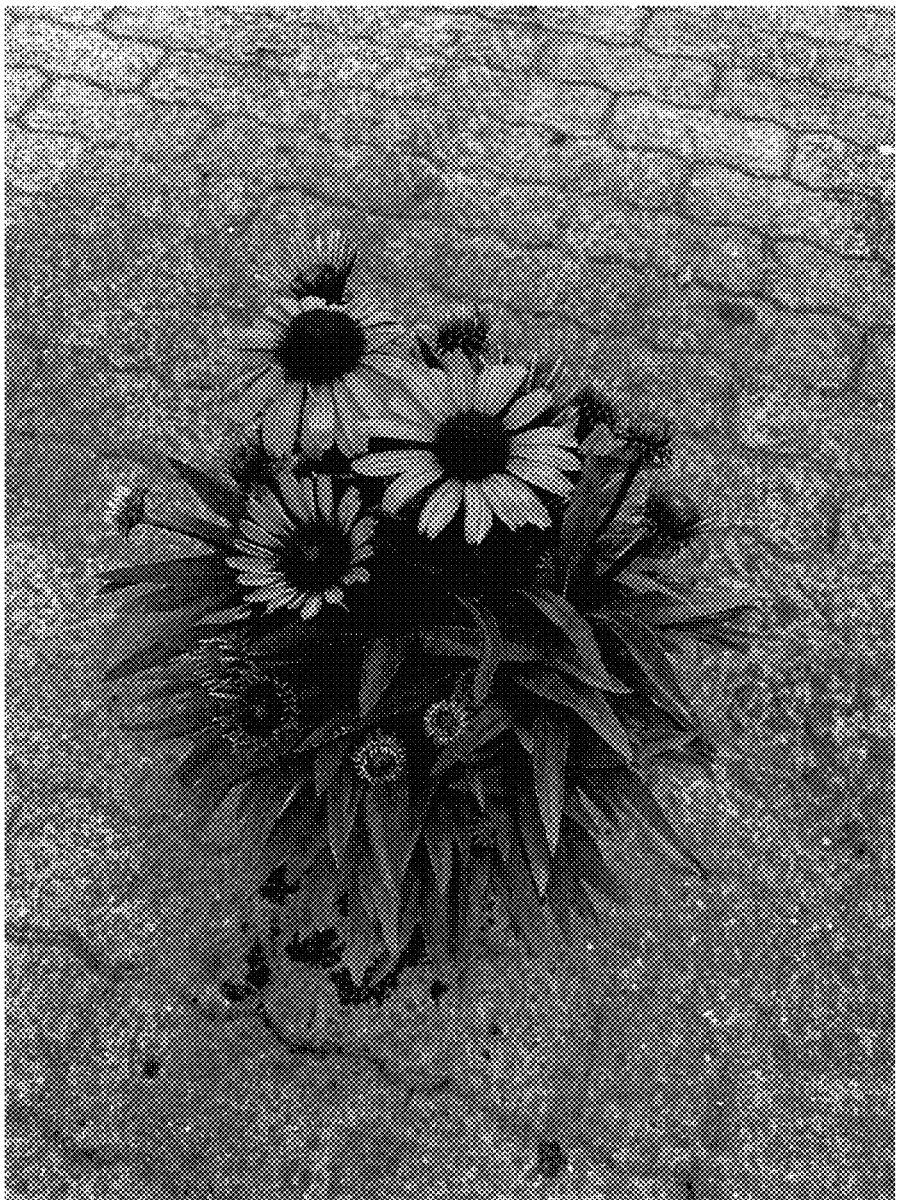

* * * * *